(12) United States Patent
Hoclet

(10) Patent No.: US 7,525,321 B2
(45) Date of Patent: Apr. 28, 2009

(54) SENSOR AND ASSEMBLY FOR HYDROMETRIC MEASUREMENTS

(75) Inventor: Michel Hoclet, Orsay (FR)

(73) Assignee: Commissariat a l'Energie Atomique (FR)

( * ) Notice: Subject to any disclaimer, the term of this patent is extended or adjusted under 35 U.S.C. 154(b) by 0 days.

(21) Appl. No.: 10/578,931

(22) PCT Filed: Nov. 19, 2004

(86) PCT No.: PCT/FR2004/050604

§ 371 (c)(1),
(2), (4) Date: May 8, 2006

(87) PCT Pub. No.: WO2005/052561

PCT Pub. Date: Jun. 9, 2005

(65) Prior Publication Data

US 2007/0079646 A1    Apr. 12, 2007

(30) Foreign Application Priority Data

Nov. 20, 2003    (FR)    ................... 03 50861

(51) Int. Cl.
*G01R 27/04*    (2006.01)
(52) U.S. Cl. .................... 324/643; 324/76.12; 324/664; 73/29.01
(58) Field of Classification Search ................. 324/643, 324/664, 76.12; 73/29.01
See application file for complete search history.

(56) References Cited

U.S. PATENT DOCUMENTS

| 5,233,306 | A | * | 8/1993 | Misra | 324/601 |
| 7,017,396 | B2 | * | 3/2006 | Mouhasseb | 73/73 |
| 7,176,697 | B1 | * | 2/2007 | Dahan | 324/643 |

FOREIGN PATENT DOCUMENTS

DE    3134662    3/1983

\* cited by examiner

*Primary Examiner*—Vincent Q. Nguyen
(74) *Attorney, Agent, or Firm*—Baker & Hostetler, LLP

(57) ABSTRACT

A device for taking ultra-high frequency hydrometric measurements by generating sine wave trains of incident wave(s) at frequencies assuming several values in arithmetic progression between a few MHz and a few GHz, and has at least one ultra-high frequency cable. The cable includes at least two measuring stations (4) spaced along the cable a predetermined distance apart, each measuring station (4) having a measuring cell (14) and a separator device capable of only sampling a portion of the incident wave(s) with sufficient energy for each measuring cell to send back an echo measurable by electronic read-out device so that the sampling of the incident wave(s) by each measuring station occurs essentially simultaneously. Each measuring cell (14) consists of an ultra-high frequency line portion with its distal end terminated by a short circuit and with the line portion having a circumferential external wall which is either porous or provided with ports.

18 Claims, 3 Drawing Sheets

SENSOR AND ASSEMBLY FOR HYDROMETRIC MEASUREMENTS

FIELD OF THE INVENTION

An aspect of the invention described herein is a distributed device for hydrometric measurements, formed with electronic means capable of generating a ultra-high frequency excitation signal, with a transmission line, with measuring cells connectible in series on this transmission line, and with electronic means for processing the reflected signals. Another aspect is the processing of hydrometric measurements from the previous transducers.

Another aspect of the invention described herein is the separation between the active electronic components generating the excitation signal and processing the reflected signals on the one hand, and the passive components such as the transmission line and the measuring cells which may be placed under hostile notably temperature or radiation conditions.

BACKGROUND OF THE INVENTION

The term "ultra-high frequency cable" is herein defined as a cable for which the dimensions of the conductors and the dimensions and characteristics of the dielectric between these conductors are adequate so that this cable has a characteristic impedance of constant value in a wide frequency range extending from a few MHz to several GHz. Its structure may be coaxial, shielded bifilar or unshielded bifilar. Such a cable is used for producing the transmission line of the measuring device according to the present invention.

Here, hydrometry refers to the measurement of the humidity content of a solid substance. If the simplest method for measuring this content, consists of picking up a sample of the material, of drying it and measuring its loss of mass, it is not always feasible as it is not always possible or desirable to proceed with such samplings.

To avoid this drawback, a method has been developed for several years, consisting of sending electromagnetic waves into the test material, based on the large dependence of permittivity on humidity content of the material for high frequencies, as permittivity of water is much larger than that of bodies such as clay which it may impregnate. The scientific foundations of the method have been described in several publications, on which we shall not elaborate in detail.

Among these methods, those based on the measurement of permittivity in the high frequency domain, approaching from lower frequency values, the relaxation frequency of water, i.e., 30 GHz at room temperature, may be considered as being close to the invention. They consist of sending a ultra-high frequency signal into a coaxial line, the dielectric of which (for example air) is replaced at the transducer by a material sample (for example clay) in hydric equilibrium with material, the water content of which is intended to be measured. The results are generally provided by comparison with tables of theoretical and/or experimental results.

However a problem occurs in that it is not easy to devise in concrete terms a layout which allows the power conveyed by the incident signal to be distributed among several sensors so that each of the latter sends back a sufficient signal to be analyzed, without picking up an excessive portion of the total signal, and to our knowledge, none of the prior art achievements manages to do this. Indeed, electromagnetic properties of the material to be measured lead to reflection of the quasi-totality of the incident wave, which precludes any mounting of several transducer cells in series. Further, even if one manages to distribute the excitation energy among different transducers, it is very difficult to limit interferences between these potential transducers. This limitation is very disadvantageous, because many applications require that several simultaneous measurements be conducted in different places of a site without having to multiply the equipment used.

In the present state of the art, digitization of signals which have traveled through the ultra-high frequency cable, cannot be directly performed for frequencies ranging up to several GHz. A frequency changing step should then be performed beforehand by techniques known to one skilled in the art (multiplication of one frequency $F_1$ by a frequency $F_2$ and then selection of the frequency band $F_1$-$F_2$).

The electronic means capable of generating sine wave trains at frequencies assuming several values in an arithmetic progression between a few MHz and a few GHz, should be as stable as possible. Preferably they consist of a quartz-stabilized frequency synthesizer. They may optionally consist of a wobbulator which we shall reconsider later.

The measurement signal is applied to vector voltmeters capable of performing the change in frequency, filtering, digitizing, digital filtering, and determining the real and imaginary components of permittivity. A digital processing operation known to one skilled in the art may be added as a complement, notably for correlation with tables of pre-recorded measurements.

A simplified means for achieving excitation and read-out of the signals consists of using a network analyzer, as this will be seen in our detailed description of the operation. Such an apparatus, well known to one skilled in the art, further includes a vector voltmeter $V_R$ forming a channel for measuring a reference voltage at the output of the electronic means generating the excitation signal. With such a measurement, it is possible to standardize the signals, i.e., get rid of constant parameters which notably depend on the ultra-high frequency cable and interconnection devices. Finally, a network analyzer has digital computation possibilities.

The separator device capable of sampling from the incident wave only a portion with sufficient energy, is normally designed so as to pick up just sufficient energy so that the measuring cell sends back an echo which may be measured by the electronic read-out means, i.e., a few µW in the present state of the art of measuring apparatuses, on which comments will be made subsequently. More generally, separator devices should be designed so that the proportion of energy which they direct towards the measuring cell is at least equal to the minimum amount of energy which this cell requires.

In reality, each measuring cell does not pick up a constant amount of energy but a constant proportion. And the functional constraint to be observed is to make sure that the cell the most away from the source receives at least the minimum amount of energy ensuring measurement performances. As the ultra-high frequency wave travels through the different measuring cells, its energy decreases and the proportion of this energy picked up by each separator must be changed if an optimized hydrometric measurement system is desired which only picks up the required minimum from this wave.

Now, functionally, if the measuring device comprises many cells, it is obvious that the first cell will only pick up a very small percentage of the incident energy, while the last one may pick up the major portion of it. As the dimensional characteristics of a cell determine the energy percentage which it will pick up, an optimized hydrometric measurement line should include cells which are all slightly different.

Nevertheless, the making of the distributed hydrometric sensor may be simplified by choosing in a suboptimal way to make separator devices which pick up from the ultra-high frequency wave, an amount of energy larger than that which they are normally designed for. A restricted number of dimensional alternatives of the separator devices used or even separator devices which are all identical at each measuring station, may thereby be obtained, which lowers the cost of the whole of the distributed hydrometric sensor.

The making of this separator device may resort to all the known means in the field of ultra-high frequencies, notably to power separators with two very dissymmetrical outputs. In this case, it is sufficient to connect to the lower power output, a simple measuring cell operating as a dead end.

In the other cases, which correspond to the preferential embodiment, this separator which performs the dissymmetric sampling of energy of the ultra-high frequency wave is made by simply juxtaposing dielectric media with different characteristics, and notably of the same nature but with different sections, this for a constant characteristic impedance.

Let us explicit this in the case when the cable is coaxial. Let us call $d_i$ and $d_e$ the inner and outer diameters of the dielectric of the ultra-high frequency cable. Diameter $d_i$ is also the diameter of the core of the cable, and diameter $d_e$ is also the inner diameter of the peripheral shielding conductor. Let us call $d'_i$ and $d'_e$ the corresponding diameters of the shrinked cable, and $d''_i$ and $d''_e$ the corresponding diameters for the measuring cell placed around the shrinked cable. The necessary operating conditions may then be expressed simply by:

$$d'_i < d_i$$

$$d_i < d'_e < d_e$$

$$d''_i < d_e$$

$$d''_e \geq d_e$$

Further, the proportion of energy entering the measuring cell will depend on the proportion of dielectric surface of the cell (or if there is a dielectric washer which precedes it, on this dielectric washer) facing the crown-shaped section of the dielectric of the ultra-high frequency power cable, i.e., as a function of the ratio:

$$(\pi/4)(d_e^2 - d_i^2)$$

$$(\pi/4)(d_e^2 - d''_i^2)$$

Analogously, the proportion of energy entering the shrinked portion of the ultra-high frequency cable is a function of the ratio:

$$(\pi/4)(d_e^2 - d_i^2)$$

$$(\pi/4)(d'_e^2 - d_i^2)$$

Moreover, in order to retain the same characteristic impedance, preferentially set to 50 Ohms, the ratio between diameters $d_i$ and $d_e$ of the ultra-high frequency cable is the same as the ratio between diameters $d'_i$ and $d'_e$ of the shrinked cable from the moment that the dielectrics have the same permittivity index.

In the case when the ultra-high frequency cable is bifilar and shielded, transposition is immediate, provided that the outer diameter of the insulator $d'_e$ of the shrinked cable is wider than the distance separating the most remote points of both conductors in a transverse cross-section of the main ultra-high frequency cable, this distance may then play the same role as $d_i$, although the calculations of the facing sections then have to be corrected accordingly.

In the case when the ultra-high frequency cable is bifilar and unshielded, transposition is immediate, relatively to the previous case. On the other hand, the metal surfaces delimiting the measuring cell remain perfectly connected to each other all around the axis of the cable, but are not electrically connected to anything else.

SUMMARY OF THE INVENTION

To satisfy these requirements, the invention relates to a distributed hydrometric sensor including:
  electronic means capable of generating sine wave trains at frequencies assuming several values in an arithmetic progression between a few MHz and a few GHz,
  at least one ultra-high frequency cable, as defined earlier, along which at least two measuring stations are found, each measuring station having a separator device capable of only sampling from the incident wave a portion with sufficient energy so that the measuring cell sends back an echo which may be measured by electronic read-out means on the one hand, and an actual measuring cell consisting of a portion of ultra-high frequency line on the other hand, the distal end of which is terminated by a short circuit, this line portion having an external wall either porous or provided with ports, and with its dielectric substantially consisting of homogeneous dielectric material sample, for which permittivity is a monotonous function of hydrometry in the relevant measurement range;
  read-out electronic means with which, from signals having traveled through the ultra-high frequency cable, these signals may be digitized, filtered in frequency, the complex reflection coefficient may be calculated in the frequency domain, a Fourier transform may be performed thereon in order to calculate the complex reflection coefficient in the time domain, and then the values of the real and imaginary parts of the permittivity may be determined so as to determine the measurement of humidity and temperature by correlation with tables of values experimentally established beforehand, by means of another hydrometric measurement method.

In accordance with the present invention to properly decouple both of the following functions: separation of the incident wave into two waves, interface between the dielectric material of the cable and the material sample in hydric equilibrium, it is preferable that each measuring cell should be preceded, in the direction of propagation of the wave, by a simple dielectric matching washer in a dielectric, preferably identical with that of the ultra-high frequency cable, and radially occupying all the space of the cavity over a certain measured length along the wave propagation axis, of the order of 5 to 15 mm. Then, the ultra-high frequency wave penetrates into the measuring cell, i.e., in a cavity with an homogeneous and suitably compressed sample of material in hydric equilibrium with the exterior medium to be measured. This suitable compression is determined experimentally.

In each of the measuring cells, the incident wave no longer propagates in a dielectric preferably identical with that of the ultra-high frequency cable, but in the sample of humidity-sensitive material. The dielectric characteristics of this material should vary according to a monotonous function of humidity in the measuring range of the sensor, and its relaxation frequency should be higher than the maximum working frequency of the measuring system. It should further be in a sufficient amount in order to give rise to a response signal with sufficient amplitude for the electronic read-out means, and suitably compressed as determined empirically. The humidity-sensitive material is preferentially clay.

According to the preferential embodiment of the present invention, the read-out means are located at the same end of the ultra-high frequency cable as the means for generating sine wave trains, and connected to this ultra-high frequency cable by a directive coupler known to one skilled in the art. The ultra-high frequency cable is then used in reflection.

According to this first alternative, which uses the ultra-high frequency cable in transmission, it is possible to measure both the signal injected at the input of the cable and the signal transmitted to the distal end. With this, both the reflection coefficient and the transmission coefficient of the ultra-high frequency cable may be calculated easily, with the result of a better signal-to-noise ratio of the measurements.

The reflected ultra-high frequency signal is applied to the input of a first vector voltmeter $V_A$, whereas the signal transmitted to the end of the ultra-high frequency cable is applied to the input of a second vector voltmeter $V_B$. A matched resistor is preferably connected to the terminals of the voltmeter $V_B$. Both the complex reflection coefficient and the complex transmission coefficient of the ultra-high frequency cable may thus be measured, from which the real part and the imaginary part of the permittivity are inferred by calculations known to one skilled in the art. These values are then correlated with humidity and temperature measurements, carried out with another measuring method during a preliminary calibration phase.

According to a more restricting alternative, the read-out means are located at the end of the ultra-high frequency cable, opposite to the one connected to the means for generating sine wave trains. The ultra-high frequency cable is then used in transmission. Indeed, in this case, means for measuring the ultra-high frequency electrical signal at the distal end of the cable, and downstream, means for determining the complex transmission coefficient of this cable may also be added.

According to a second alternative, which uses the ultra-high frequency cable in reflection, a single vector voltmeter $V_A$ measures the complex reflection coefficient, from which the real part and the imaginary part of the permittivity are inferred by calculations known to one skilled in the art. These values are then correlated with humidity and temperature measurements carried out by another measuring method during a preliminary calibration phase.

For both of these alternatives, their achievement in practice imposes that another vector voltmeter $V_R$ performs the measurement of a reference voltage at the output of the electronic means generating the excitation signal, this measurement being used for standardizing the signal, i.e., getting rid of constant parameters notably dependent on the ultra-high frequency cable and on the interconnection devices.

In the ultra-high frequency domain, it is generally advantageous to get rid of parasitic reflections at the distal end of a line by placing an adapted load at its distal end. Here it is advantageous and natural to connect the distal end of the ultra-high frequency cable to a load having an impedance substantially equal to the characteristic impedance of this cable. But this is not mandatory because of how the invention actually works: an unmatched end, such as for example an open air end (unconnected), is expressed by an extremely strong reflected signal but which arrives after the useful signals and may therefore in fact be separated. On the other hand, an unmatched end from the point of view of impedance would risk saturating certain circuits because of this amplitude of the reflected signal.

To achieve hydric equilibrium between the inside of this cell, and the exterior medium to be measured, the invention has two alternatives. According to the first alternative, the metal wall includes ports or slits, preferably directed longitudinally along the axis of the ultra-high frequency cable in order to perturb the current lines as less as possible.

According to the second alternative, the external wall of this line portion is porous, made by sintering stainless metal, such as stainless steel, certain bronzes or titanium.

The conducting metal surfaces used for the cables and delimiting the measuring cells are preferentially in copper.

Alternative Separators and Cells:

Let us refer back to the separator device capable of sampling from the incident wave only a portion with sufficient energy, and to how to combine it with various types of ultra-high frequency cables.

The preferential embodiment of a measuring cell according to the invention varies very little according to whether the ultra-high frequency cable is coaxial or bifilar and shielded ($1^{st}$ and $2^{nd}$ embodiments).

The first embodiment corresponds to a coaxial cable, and is characterized in that the measuring cell has a structure coaxial with the ultra-high frequency cable ensuring operation of the measuring cell located downstream, and around the latter cable which then has, at the place of the cell, a sudden narrowing with constant impedance. It is also characterized in that the separator device is made by simply juxtaposing dielectric media at the place where the ultra-high frequency cable is replaced, by putting two media in parallel: a dielectric providing continuity of the cable on the one hand, the measuring cell on the other hand, or the dielectric matching washer if there is one.

This first embodiment may further be defined in that the measuring cell forms a hollow cylinder delimited by three metal conducting surfaces in contact: an inner cylindrical surface, an outer cylindrical surface and a planar disk at the distal end. This hollow cylinder is coaxial with the ultra-high frequency cable and placed around it, the latter having at this place, a sudden narrowing of the dielectric and of the outer conductor, the dimensions of these components being nevertheless selected so that the characteristic impedance remains as constant as possible, before, during and after the narrowing. It is obvious that in order to keep the characteristic impedance of the cable constant, when the diameter of the dielectric is suddenly reduced, the diameter of the conducting core should simultaneously be reduced in proportions known to one skilled in the art.

The second embodiment corresponds to a ultra-high frequency cable with a shielded bifilar structure. The section of this cable then no longer includes a central core but two conductors placed symmetrically relatively to the plane of symmetry of this section. Both conductors are surrounded by a dielectric, itself surrounded with a conducting shield. At each measuring cell, this dielectric has a smaller diameter, limited by a conducting cylindrical surface section which forms both the shielding of the thereby shrinked line and the internal wall of a measuring cell in the shape of a hollow cylinder, identical with the one described in the case of a coaxial ultra-high frequency cable. The external wall of this cavity consists of a second conducting surface section either porous or including ports allowing hydric equilibrium with the surrounding medium, itself also electrically connected to the shield of the ultra-high frequency cable. This cavity preferably contains a dielectric washer extending radially between both conducting surfaces, this portion preferentially being of the same material as the ultra-high frequency cable, preferentially with structure continuity. The remainder of the cavity, up to the short circuit distal metal washer, forms the measuring cell filled with the material sample in hydric equilibrium with the medium to be measured.

A third embodiment of a measuring cell according to the invention, uses a ultra-high frequency cable of the unshielded bifilar type, i.e., consisting of two separate conductors surrounded by a dielectric which may have a flattened shape. The measuring cell is at least partly located in the thickness of this dielectric, and assumes a shape similar to the measuring cells, as described earlier, except that it is not electrically connected to anything. If the section of the ultra-high frequency cable exhibits a dielectric, the outer contour of which is flattened, for example in an oval shape, the measuring cell may in turn be flattened, for example in an oval shape.

A fourth embodiment corresponds to the case when the separator device is no longer closely associated with the measuring cell but resorts to any ultra-high frequency device, notably a power separator with two very dissymmetrical outputs. As an example, this separator is a T- or Y-coupler, one of the outputs of which receives much more power than the other. This output is then connected to a ultra-high frequency cable section comparable to the cable transmitting the main part of the ultra-high frequency wave, and terminated by a simplified measuring cell which does not include any shrinked cable in its middle. The central conductor is then no longer a cylindrical conducting surface but a simple conducting wire, preferably in copper, the distal end of which is connected to a conducting disk closing the cell.

In all these cases, the measuring cell according to the invention may be made in a large variety of waves and shapes, from the moment that the above constraints are observed, and notably a short circuited line portion has its dielectric suddenly replaced with a material sample in hydric equilibrium with the medium to be measured. It is designed so as to have an impedance not very different from the one of the ultra-high frequency cable which powers it. If the cell, as this is generally the case, has a diameter larger than that of the bypass cable, the ultra-high frequency wave propagating in the dielectric of the cable should be brought into this area of larger diameter by means of an intermediate dielectric part before directly contacting the material sample in hydric equilibrium.

Operation:

It is now possible to understand the operation of the separator device capable of sampling only a portion of the incident microwave when it is closely associated with the measuring cell as in the first three embodiments. The incident wave propagating in the dielectric of the ultra-high frequency cable sees, upon reaching the measuring station, a central area provided with a dielectric comparable to that of the cable, a peripheral area consisting of the actual measuring cell, both of these areas being separated by a conducting surface electrically connected to the peripheral conductor of the ultra-high frequency cable, and the power being distributed between both of these areas according to their respective sections.

The respective sections of the dielectrics corresponding to both of these media are selected according to the proportion of incident energy which is intended to be retained in the downstream portion of the ultra-high frequency cable, and therefore to the number of transducers downstream. This selection should however provide each measuring cell with minimum energy so that the return signal may be read out with a sufficient signal-to-noise ratio. For setting up a distributed hydrometric sensor according to the invention, it is therefore necessary to determine the ratio which is estimated as being optimum, between the number of measuring stations and the accuracy of the signal.

Independently of the embodiment of the measuring cells, excitation of the ultra-high frequency cable connected to the measuring cells may be performed in different ways. Each way should submit this cable and the measuring cells to a plurality of signals covering a plurality of frequencies, close to each other, the whole covering a band of frequencies ranging from a few MHz to several GHz.

The most simplest way consists of generating the excitation ultra-high frequency wave, by a very stable frequency synthesizer, controlled by a quartz. It is also possible to use a wobbulator, i.e., a generator of sine waves over a small time scale, but with a frequency which continuously varies from a minimum value to a maximum value, or vice versa. Nevertheless, with such a method, it is not possible to perform on the read-out signal, frequency filtering over a band as narrow as when one resorts to a frequency synthesizer. The signal-to-noise ratio of the measuring device is subject to a penalty.

Preferentially, in order to improve the signal-to-noise ratio, one opts for applying a same sine frequency for sufficient time in order to establish an equilibrium state, and then a new frequency is selected and the operation is repeated, and so forth. Thus, at each instant, excitation is performed on an extremely narrow frequency band, which allows more efficient filtering of the received signal. This filtering is performed all along the ultra-high frequency chain, several times as customarily practiced in this technique. Narrowest filtering is performed digitally, just after digitization. To obtain good performances, it is performed with a narrow band: a few tens of Hz, or even a few Hz.

Finally, a third method more suited to laboratories, would consist of generating excitation pulses as close as possible to Dirac pulses, with which the frequency response of the measuring system may be measured. This will not be developed here as this is known to one skilled in the art, on the one hand, and it is badly suited to industrial applications on the other hand.

The preferential way consisting of applying a same frequency for a sufficient time and then changing this frequency, may be described in more detail as follows.

The successive excitation frequencies $f_i$ are selected so as to form an arithmetic progression when i varies, and this so that the Fourier transform may be calculated. According to our embodiment, 1,601 measurement points are placed in arithmetic progression between a minimum frequency of 3 MHz and the maximum frequency of 6 GHz.

The time interval between two successive sine trains should be sufficiently long so as to allow the establishment of a permanent state in which the excitation signal and the echo sent back by each measuring cell coexist. By distinguishing each echo, it is possible to localize the cell which generated it. As an indication in our preferential embodiment, described later on, this time between two successive sine wave trains is 187.5 ms.

When each of the measuring cells of the system is submitted to these excitation waves, it is the center of damped oscillations between the bottom and the entrance of this cell, each reflection on the entrance of the cavity giving rise to emission of an oscillation which returns towards the source.

The Fourier transform of this response, with which one may pass from the frequency to the time domain, is easy to interpret. Each measuring cell thereby generates a reflected signal illustrated as a function of time by a succession of equidistant peaks, with decreasing amplitudes forming its signature. This constant distance allows the real part of the permittivity $\epsilon(\omega)$ of the cell to be determined, which is related to the humidity content.

Theoretically, if this cell has a length <<l>> along the direction of the wave vector, the path that this ultra-high frequency wave should cover in the cell is $n_{2l}$, where n is the refractive index of the material sample. If the extinction or damping coefficient χ is not insignificant, as upon approaching the water transition frequency (approximately around 4 to 5 GHz and above), the sought-after real $\epsilon'_r$ and imaginary $\epsilon''_r$ components of the permittivity $\epsilon(\omega)$ are given by:

$$n+j\chi=\sqrt{\epsilon(\omega)}=\sqrt{(\epsilon'_r+j\epsilon''_r)}.$$

In practice, when the maximum working frequency is far from the water relaxation frequency (approximately below 1 GHz), it is sufficient to consider that the refractive index for a line section or a cell of length l is related to the real components $\epsilon'_r$ by:

$$n_1=\sqrt{\epsilon'_{rl}}$$

The theoretical relationship shows the link between the line damping coefficient and the imaginary part $\epsilon'_r$ of the permittivity $\epsilon(\omega)$, itself related to temperature.

The quantities which characterize the material to be measured are humidity and temperature. The quantities characterizing the signal of the sensor are the distance between the observable lines in the time representation of the signal having traveled through the cable, which is principally related to the real permittivity, and the relative amplitude of each line of the signal of a sensor, which are principally related to the conductivity of the sensitive material and therefore to its imaginary permittivity. Complete calibration of a sensor should take into account these four quantities, i.e., determine from both characteristics of the signal, both of the characteristics of the material.

The line portions separating two successive transducers may a priori generate, with the echoes conveying useful information, products of parasitic inter-modulation; in practice, as the invention considerably limits the amplitude of the echo conveying the useful information (relatively to a resonant cavity from the prior art), these inter-modulation products are so small that they are mingled with background noise.

Read-out of the hydrometry and temperature values can only occur after a preliminary calibration phase, which is carried out by means of another measurement method such as the drying of samples, as already mentioned. The actual read-out of the hydrometry and temperature values is carried out experimentally by correlation with tables of results obtained during the calibration phase.

These measurements are related to the water content and to the temperature by known equations of electromagnetism. A vector voltmeter or a network analyzer such as for example HP8753B from Hewlett Packard may also be used, which directly gives the real part and the imaginary part of the received signal. For more information, reference should be made to Hewlett-Packard's Application Note, Test and Measurement Application 95-1 designated as: <<S-parameter techniques>>, chapter 6: <<Measurement of S-parameters>>.

However, as the calculations are lengthy, read-out of the water content and temperature measurements is preferentially carried out experimentally by correlation with tables of results obtained beforehand, in a calibration phase, by means of another measurement method such as the drying of samples, as already mentioned.

The calibration varies with the characteristics of each measuring cell, notably the dimensions of the dielectric in the portion where it is narrowed and the dimensions of the transducer cavity, as well as the nature of the dielectric. The calibration carried out on a measuring cell therefore remains usable for another measuring cell which has these characteristics in common.

When several ultra-high frequency cavities are thus placed in different measuring stations, in series on a ultra-high frequency cable, each one of them sends back its own signature but with a time lag depending on the distance from the excitation source. It is then easy to distinguish the response of each measuring cell.

The ultra-high frequency cable portion located between two successive transducers, itself, also behaves as a ultra-high frequency line portion for which the end is the discontinuity introduced by the next measuring cell. It therefore operates in turn as a ultra-high frequency cavity even if this is less marked. But the weakness of the energy picked up by each transducer practically reduces the amplitude of such echoes to an insignificant value.

BRIEF DESCRIPTION OF THE DRAWINGS

The invention will now be described in connection with the accompanying figures of which.

DETAILED DESCRIPTION OF THE PREFERENTIAL EMBODIMENT

Figure 1:
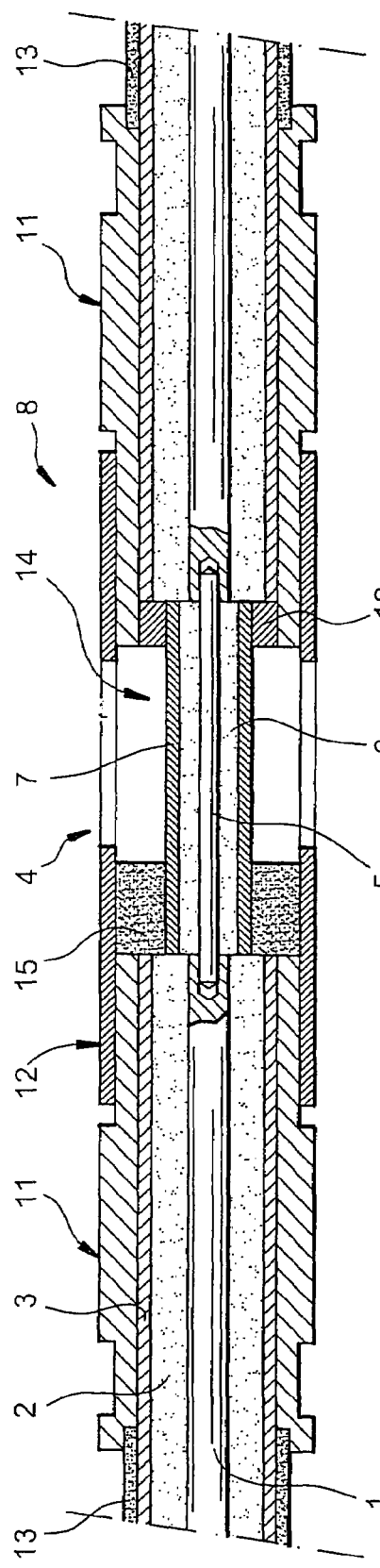
FIG. 1 schematizes a preferential embodiment of a transducer device according to the invention, consisting of a separator and a measuring cell associated with each other, wherein this measuring cell is of the coaxial type, mounted on a coaxial cable.

FIG. 1 schematizes an embodiment of a transducer device consisting of a separator and a measuring cell associated with each other, wherein this measuring cell is of the coaxial type, mounted on a coaxial cable. This cable comprises in the centre an electrically conducting core 1 with diameter $d_i$, which is wrapped up in a Teflon dielectric sheath 2, and a peripheral conductor 3, here consisting of a copper tube with an inner diameter $d_e$, but which may be copper braiding in other embodiments. It is surrounded by an insulating and protective sheath 13.

According to the invention, this coaxial cable is suddenly narrowed at the measuring cell 14 which measures the humidity of the surrounding material in which the cable is buried, such as clay for confining nuclear fuel waste. In this case, the distance between two consecutive measuring cells is about one meter. For an experimental set-up, one opted for achieving associations of one measuring cell and one separator as distinct components of the ultra-high frequency cable, connected to it on either side by miniature coaxial connectors of the SMA type. The shrinked ultra-high frequency cable section includes a core 5 with an outer diameter $d'_i$, which sinks into the central ports of the connectors placed on either side, a dielectric 6 itself also in Teflon, and a tubular conductor 7 made with a piece of copper tube, with an inner diameter $d'_e$ of the order of 2.4 mm, less than the inner diameter $d_e$ of the peripheral conductor 3 of the ultra-high frequency cable located on either side. The latter constraint is required so that the energy flowing in the dielectric of the ultra-high frequency cable may be distributed among the downstream portion of this same cable and the measuring cell. As the insulators of the cables thus are in Teflon in order to retain the same characteristic impedance, set to 50 Ohms, the ratio between the diameters $d_i$ and $d_e$ of the ultra-high frequency cable is the same as the ratio between the diameters $d'_i$ and $d'_e$ of the shrinked cable.

The proportion of the energy of the ultra-high frequency wave sent by the separator towards the measuring cell 14 or the dielectric matching washer 15 which precedes it, is determined by the common surface between the cross-section of the dielectric 2 and the left cross-section of the cell 14 or of the dielectric matching washer 15. It is determined in such a way that the echo emitted in return towards the read-out means reaches the latter with a power of the order of one to 2 µW.

The coaxial components 11 which provide the electric continuity are commercial coaxial connector components for which the illustration of the stuffing box is not detailed.

With this arrangement, the incident excitation wave emitted to the left of the coaxial cable and propagating in the dielectric 2, upon reaching the measurement station 4, almost completely crosses the latter by passing through the shrinked ultra-high frequency cable portion 5, 6, 7; but a very small portion of the power of the incident wave, of the order of 1 to 2 µW, is transmitted out of the envelope section 7 and therefore passes into the dielectric matching washer 15, and then into the measuring cell 14 filled with a clay sample.

The electrically conducting ring 10, establishes a short circuit between the tubular conductor 7 and the outer tubular conductor 12 at the distal end of the measuring cell 14 so as to have it operate as a ultra-high frequency resonant cavity. FIG. 1 shows that these components 10 and 12 are in electrical contact via the coaxial connector body 11. It is obvious that both of these parts only form for the measuring cell 14, a single conducting planar surface extending radially. The portion of the waves arriving in this cavity is reflected on the distal short circuit, returns to the junction between the dielectric 2 and the measuring cell 14. There, a small portion of this wave passes through this junction and returns to the entrance of the cable where it is analyzed, whereas the major portion of this wave is reflected and returns into the cavity where it is again reflected on the distal short circuit, and so forth until this wave is damped.

The connecting socket 8 may directly play the role of the male portion of the miniature coaxial connector from the moment that it has a satisfactory surface condition and that the core 5 has the diameter of the corresponding connection pin.

The portion of the incident wave propagating in the dielectric 2 and transmitted to the measuring cell 14 is determined by the common surface between the right transverse section of the dielectric 2 and the left transverse section of the cavity. It may therefore be adjusted according to the diameters of the coaxial cables used.

The discontinuities of the dielectric structures through the measuring cell 14 produce a loss of the signal which may be significant if the surfacing of the opposite faces is not perfect. It is therefore recommended that the dielectrics should be made not only from the same material but if possible with structure continuity.

The major portion of the signal has however crossed the measuring cell 14 by passing through the dielectric 6; it subsequently reaches another measuring station 4, located further down on the cable, and similar to the one which is illustrated, and similar phenomena occur there. A line of more than about ten measuring cells may thereby be achieved easily, the limit mainly depending on the performances of the read-out device. If it is desired to optimize the performances of such a measurement system, including a large number of cells, it is preferable to gradually change the proportion of the incident power sent into the measuring cell, as discussed earlier.

To simplify the implementation and to benefit from processing capabilities, we used as a means for producing the excitation and read-out of the signals, a Hewlett Packard network analyzer of the HP 8510 type. Such an apparatus includes a frequency synthesizer used for generating the excitation signals. It also includes three vector voltmeters $V_A$, $V_B$ and $V_R$, the third forming a channel for measuring a reference voltage picked up in parallel at the beginning of the ultra-high frequency cable by means of a ultra-high frequency power coupler. The other measurement channels are coupled with the cable in the same way, channel A with the origin of the ultra-high frequency cable, and channel B, only used during transmission experiments, with the distal end of the cable.

Several filtering operations, internal to the apparatus, optimize the measurement. After digitization a frequency change of the useful signal is carried out with a frequency F2 which differs from the initial frequency F1 by 10 kHz. Several other adjustments were attempted, including pass-bands of a few Hz.

The end of the line, terminated on a matched load, does not send back any echo. But tests were also carried out with mismatched loads.

The network analyzer may therefore measure the wave reflection coefficient $S_{11}(\omega)$ at the entrance of the line by its real component and its imaginary component with which it is possible to calculate the real and imaginary permittivity values, $\epsilon(\omega)$ and $\mu_r(\omega)$ for each measuring cell.

The signal-to-noise ratio of the measurements depends on the signal-to-noise ratio of the analyzer, which is $10^5$. However, in practice, inhomogeneities of the cable send back a constant background noise which reduces the signal-to-noise ratio to an effective value of $10^4$. Further, when the signal to be measured becomes too weak with respect to the input characteristics of the analyzer, the signal-to-noise ratio falls.

Figure 2:
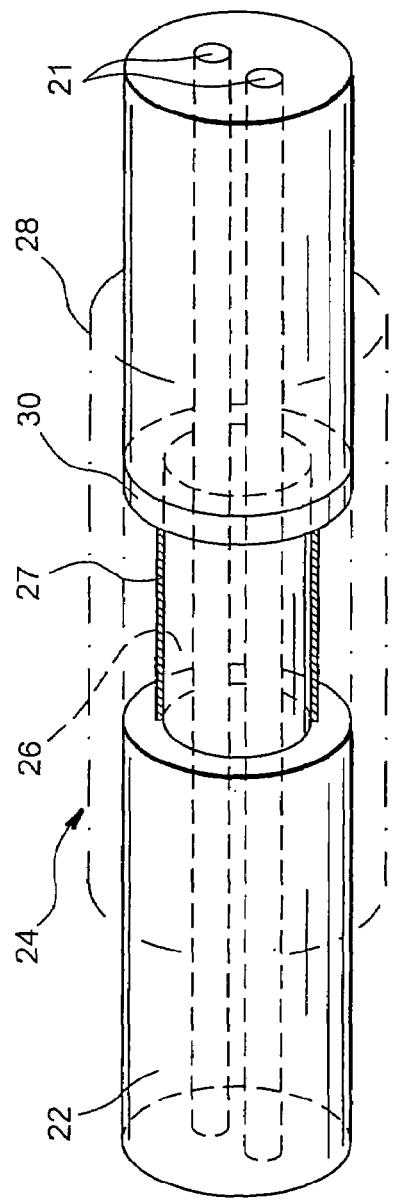
FIG. 2 schematizes a second embodiment, a preferential embodiment of a transducer device according to the invention, consisting of a separator and a measuring cell associated with each other, using a shielded bifilar cable.

FIG. 2, schematizes an alternative embodiment of a transducer device according to the invention, consisting of a separator and a measuring cell associated with each other, using an unshielded bifilar cable, wherein the ultra-high frequency cable is made as a shielded bifilar cable, and where the measuring cell retains its coaxial structure. The core is simply replaced with two conductors sufficiently close to each other relatively to the outer diameter of the dielectric.

This measuring cell is then made up from the ultra-high frequency cable comprising a pair of identical conducting cores 21 and a dielectric 22, the periphery of which is removed by machining at the measuring cell 24 so as to only leave a reduced dielectric section 26. A conducting envelope section 27 is then positioned around the dielectric section 26, as earlier, and then a conducting ring 30 at the distal end of the thereby formed cavity, before positioning a connecting socket 28 similar to the socket 8 already encountered around the cable at the location of the measuring cells according to the preferential embodiment. It is obvious that the encountered electromagnetic phenomena are the same.

Figure 3:
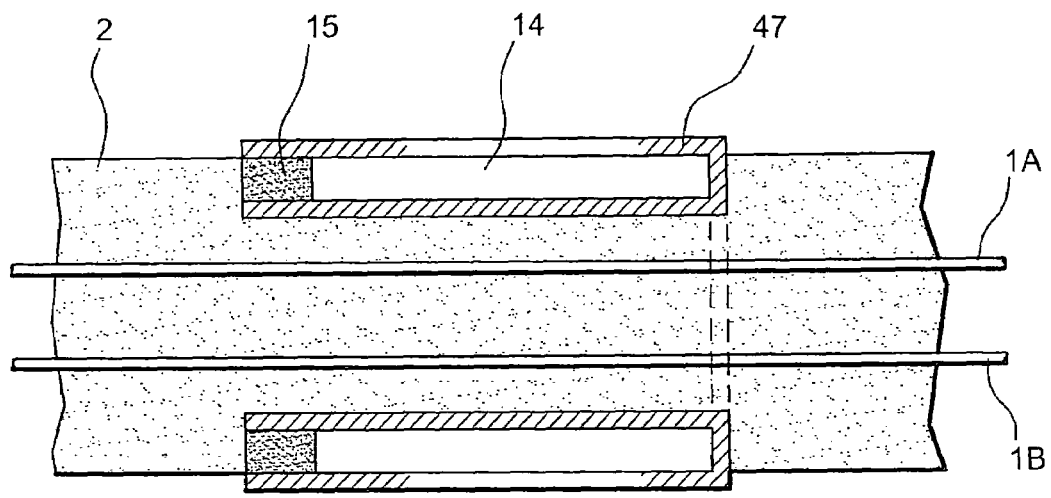
FIG. 3 schematizes another embodiment of a transducer device according to the invention, consisting of a separator and a measuring cell associated with each other, using an unshielded bifilar cable.

FIG. 3, schematizes an alternative embodiment of a transducer device according to the invention, consisting of a separator and a measuring cell associated with each other, using an unshielded bifilar cable, where the measuring cell retains its coaxial structure. Relatively to the preceding alternative, the only change is the lack of any electrical connection between the surfaces which delimit the measuring cell and both conductors of the ultra-high frequency cable. The measuring cell 14 is delimited by a metal envelope 47 and has an annular shape. Here, the conducting core comprises two parallel components 1A and 1B, which pass through the recess formed in the middle of the metal envelope 47. The metal envelope 47 and the washer 15 form a closed cavity for the cell 14.

Figure 4:
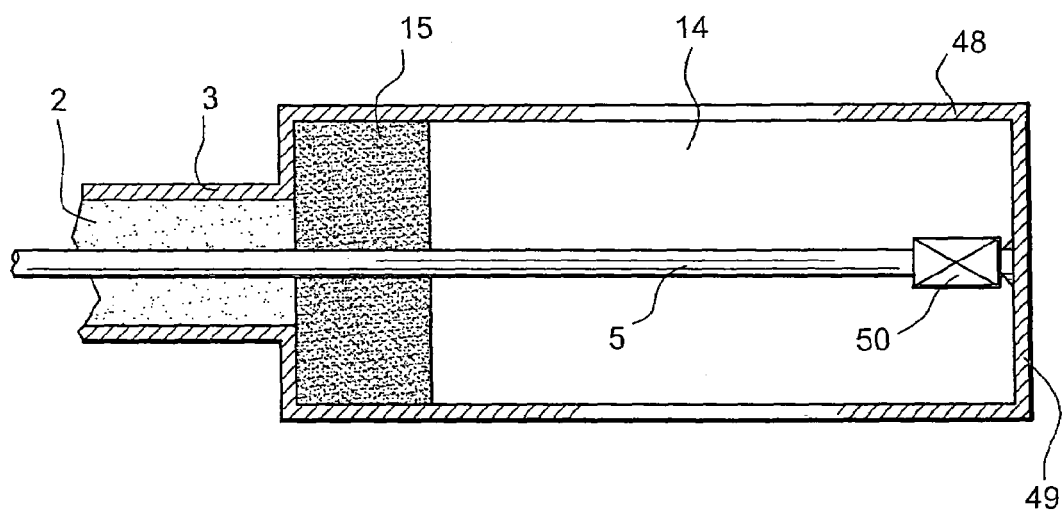
FIG. 4 schematizes a third embodiment of a simplified measuring cell according to the invention, i.e., the power separator of which consists of a Y power divider, one output of which is a measuring cell and the other output is the downstream portion of the coaxial line.

FIG. 4 is a third embodiment of a simplified measuring cell according to the invention, i.e., for which the power separator consists of a Y-power divider, one output of which is a measuring cell and the other output is the downstream portion of the coaxial line. It comprises a resistor 50 for matching the impedance of the cable placed on the core 5 at the end of the measuring cell 14. The core 5 penetrates into the measuring cell 14 and is soldered to the bottom 49 of the metal envelope 48.

The embodiments described earlier use connectors and measuring means from a microwave laboratory which are costly. For an industrial use, these means may be replaced with less costly means and for filling the same functions, such as associating an ultra-high frequency reflectrometric bridge with vector voltmeters and with directive couplers. But it is preferable to use the teachings above for designing a specific set-up schematized hereafter.

Figure 5:
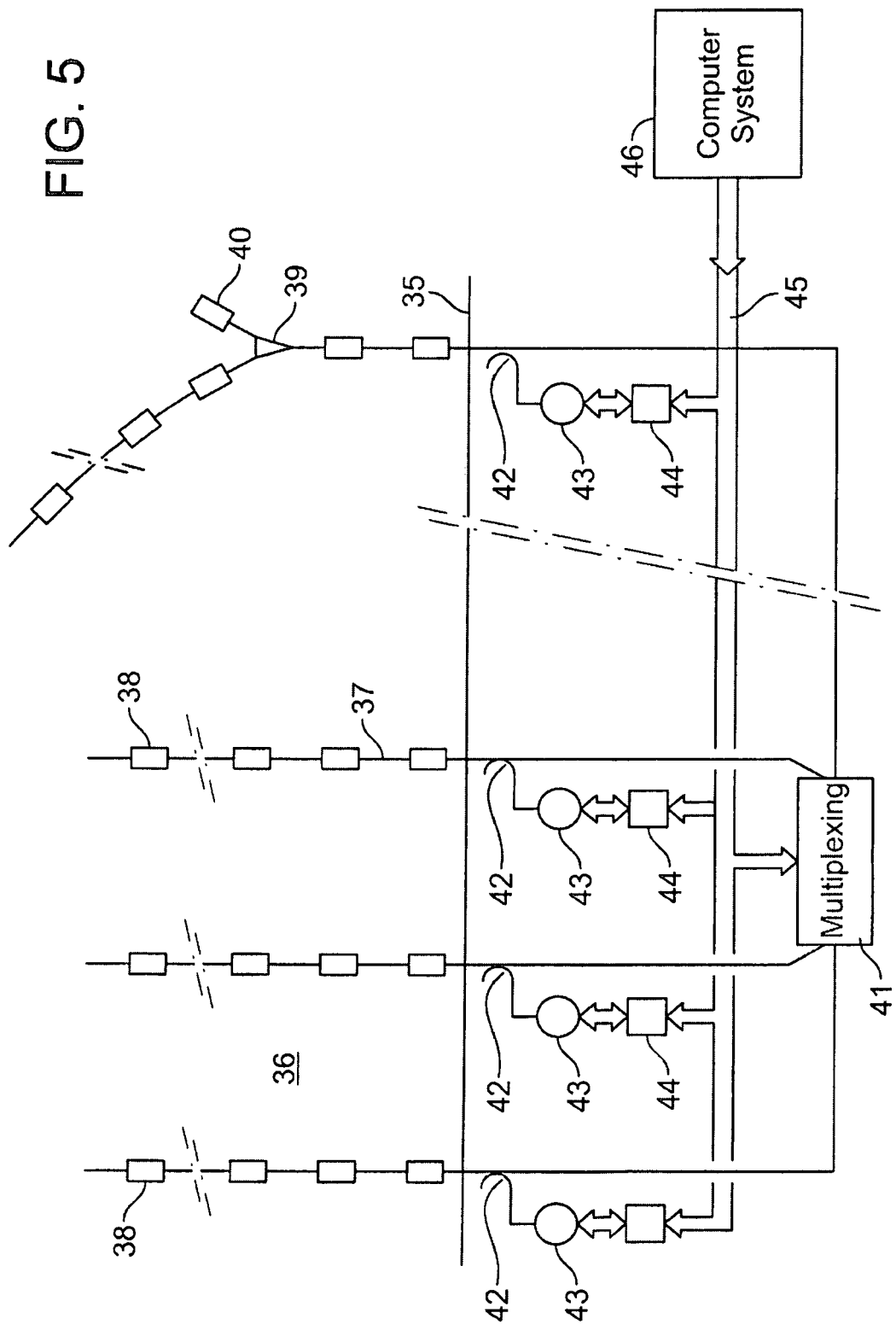
FIG. 5 schematizes a distributed device for hydrometric measurements, according to the invention.

FIG. 5, illustrates a complete embodiment of the invention. A finely worked barrier 35 confines a volume of clay 36 from the outside. A series of coaxial cables 37 penetrate therein and these coaxial cables 37, provided with transducers 38 are formed with a separator and an associated measuring cell, similar to the ones described, and cascaded. With a dissymmetrical power separator achieved by a power coupler 39, it is possible to connect one simplified measuring cell 40 to one of the lines. Each of the coaxial cables 37 is fed by a multiplexing box 41 outside the clay volume 36, with a PLL-stabilized quartz-controlled frequency synthesizer, which generates sine wave trains at frequencies which assume several values in arithmetic progression between a few MHz and a few GHz. The signals which have traveled through each cable (here, in reflection) are sampled by directional couplers 42 and applied to the input of the vector voltmeter 43 dedicated to this cable. A processing device 42 with a microcontroller is associated with each of these vector voltmeters which are connected through a bidirectional bus 45 to a computer system 46, with which the operating parameters may be determined and which receives digital values of the real and imaginary parts of the permittivity in each of the measuring cells, before carrying out the comparison with the pre-recorded measurement tables. The whole forms an exemplary distributed hydrometric measurement device according to the invention.

The invention is applied to all the cases where distributed measurement of hydrometry is required on a same cable or a set of cables connected in parallel. The high cost of the network analyzer may be reduced by producing dedicated electronics. Further, this cost is associated with a significant number of measuring stations.

The components make the invention intrinsically resistant to ionizing radiations, which makes it particularly useful for measuring the water content of clays surrounding nuclear waste containers.

The invention claimed is:

1. A device for ultra-high frequency hydrometric measurements comprising:
    electric means capable of generating sine wave trains of incident wave(s) at frequencies assuming several values in arithmetic progression between a few MHz and a few GHz,
    at least one ultra-high frequency cable including at least two measuring stations (4) within said cable spaced along the cable a predetermined distance apart from each other with each measuring station (4) having a measuring cell (14) and a separator device capable of only sampling a portion of the incident wave(s) with sufficient energy for each measuring cell to send back an echo measurable by electronic read-out means so that the sampling of the incident wave(s) by each measuring station occurs essentially simultaneously and with each measuring cell (14) consisting of a ultra-high frequency line portion the distal end of which is terminated by a short circuit, this line portion having a circumferential external wall either porous or provided with ports, and having its dielectric essentially consisting of a sample of homogeneous dielectric material for which permittivity is a monotonous function of the hydrometry in the relevant measurement domain, and
    electronic read-out means for measuring the echo sent back from each measuring cell and determining from signals having traveled through the ultra-high frequency cable, values of the real and imaginary parts of the permittivity in order to determine the measurement of humidity and temperature by correlation with tables of values experimentally established beforehand by means of another hydrometric measurement method.

2. A device for hydrometric measurements, according to claim 1, wherein the electronic read-out means include means: for digitizing these signals, for filtering them in frequency, for calculating the complex reflection coefficient in the frequency domain, for performing a Fourier transform in order to calculate the complex reflection coefficient in the time domain, and then for determining the values of the real and imaginary parts of the permittivity.

3. The device for hydrometric measurements, according to claim 1, wherein the read-out means are located at the same end of the ultra-high frequency cable as the means for generating sine wave trains, and are connected to this ultra-high frequency cable by a directive coupler.

4. The device for hydrometric measurements, according to claim 1, wherein the ultra-high frequency cable is coaxial.

5. The device for hydrometric measurements, according to claim 1, wherein the ultra-high frequency cable is shielded and bifilar.

6. The device for hydrometric measurements, according to claim 1, wherein the ultra-high frequency cable is unshielded and bifilar.

7. The device for hydrometric measurements, according to claim 6, wherein the measuring cell includes a hollow cylinder-shaped cavity delimited by:
    an inner conducting cylindrical surface, with a diameter less than the smallest diameter of the dielectric surrounding both conductors,
    an outer conducting cylindrical surface,
    the distal portion of this cavity consisting of a conducting washer putting both cylindrical surfaces into contact over 360°,
    this cavity being filled at its end turned towards generator, with a dielectric identical with the one of the cable and occupying all the space between both cylinders over a length of a few millimeters, and being filled in the remaining portion with the homogenous dielectric material sample for which permittivity is a monotonous function of the hydrometry.

8. The device for hydrometric measurements, according to claim 1, wherein the measuring cell is coaxial with the ultra-high frequency cable, and the latter has sudden narrowing at this cell.

9. The device for hydrometric measurements, according to claim 1, wherein the device capable of only sampling from the incident wave, a portion having sufficient energy, is a power divider, and the measuring cell is placed in derivation relatively to the ultra-high frequency cable.

10. The device for hydrometric measurements, according to claim 1, wherein the external wall of the measuring cell is provided with slits directed along the wave propagation vector.

11. A hydrometric measurement assembly comprising at least one sensor according to claim 10, characterized in that the generator of sine wave trains is a frequency synthesizer, the electronic read-out means are formed with a vector voltmeter (43) associated with digital processing means.

12. The device for hydrometric measurements, according to claim 1, wherein the external wall of the measuring cell is porous.

13. The device for hydrometric measurements, according to claim 1, wherein the measuring cell includes a hollow cylinder-shaped cavity delimited by:
- an inner conducting cylindrical surface, also forming the shielding of the shrinked portion of the ultra-high frequency cable,
- an outer conducting cylindrical surface, electrically connected through its two ends to the shielding of both ultra-high frequency cable sections which surround it,
- the distal portion of this cavity consisting of a conducting washer putting both cylindrical surfaces and the downstream portion of the ultra-high frequency cable into contact over 360°,
- this cavity being filled at its end turned towards the generator, with a dielectric identical with the one of the cable, and occupying all the space between both cylinders over a length of a few millimeters, and being filled in the remaining portion with the homogeneous dielectric material sample, for which the permittivity is a monotonous function of the hydrometry.

14. The device for hydrometric measurements, according to claim 1, characterized in that one or more distal measuring cells sample a larger proportion of the incident microwave than the measuring cells closest to the source.

15. The device for hydrometric measurements, according to claim 1, characterized in that the dielectric of the ultra-high frequency cable and of the measuring cell have a continuous structure.

16. The device for hydrometric measurements, according to claim 1, including a first generator of sine wave trains, a multiplexing device successively switching these wave trains to one end of several ultra-high frequency cables, a vector voltmeter (43) connected to each of these ultra-high frequency cables and electronic means with which the complex reflection coefficient may be calculated in the frequency domain, a Fourier transform may be performed in order to calculate the complex reflection coefficient in the time domain, and then the values of the real and imaginary parts of the permittivity may be determined in order to determine the measurement of humidity and temperature by correlation with tables of values experimentally established beforehand by means of another hydrometric measurement method.

17. The device for hydrometric measurements, according to claim 1, wherein the read-out means are located at the end of the ultra-high frequency cable, opposite to the one connected to the means for generating sine wave trains.

18. A hydrometric measurement assembly comprising at least one sensor according to claim 1, characterized in that the generator of sine wave trains and the electronic read-out means are formed with a network analyzer.

* * * * *